United States Patent
Brown et al.

(10) Patent No.: US 8,765,105 B2
(45) Date of Patent: Jul. 1, 2014

(54) HUMAN SEBUM MIMETICS DERIVED FROM BOTANICAL SOURCES AND METHODS FOR MAKING THE SAME

(71) Applicant: International Flora Technologies, Ltd., Chandler, AZ (US)

(72) Inventors: James S. Brown, Gilbert, AZ (US); Robert Kleiman, Sun Lakes, AZ (US); Sambasivarao Koritala, Sun Lakes, AZ (US); David Ashley, Phoenix, AZ (US)

(73) Assignee: International Flora Technologies, Ltd., Chandler, AZ (US)

( * ) Notice: Subject to any disclaimer, the term of this patent is extended or adjusted under 35 U.S.C. 154(b) by 0 days.

(21) Appl. No.: 13/685,206

(22) Filed: Nov. 26, 2012

(65) Prior Publication Data

US 2013/0183259 A1    Jul. 18, 2013

Related U.S. Application Data

(62) Division of application No. 12/911,150, filed on Oct. 25, 2010, now Pat. No. 8,343,468.

(60) Provisional application No. 61/254,909, filed on Oct. 26, 2009, provisional application No. 61/363,564, filed on Jul. 12, 2010.

(51) Int. Cl.
    *A61K 8/18*    (2006.01)

(52) U.S. Cl.
    USPC ............................................. 424/70.1

(58) Field of Classification Search
    None
    See application file for complete search history.

(56) References Cited

FOREIGN PATENT DOCUMENTS

WO    WO 0226207 A2 *    4/2002

* cited by examiner

*Primary Examiner* — Anand Desai
*Assistant Examiner* — Melissa Mercier
(74) *Attorney, Agent, or Firm* — The Noblitt Group, PLLC

(57) ABSTRACT

Human sebum mimetics and methods for producing human sebum mimetics are provided. In one exemplary embodiment, a human sebum mimetic comprises a wax ester derived from interesterification of refined botanical oil comprising palmitoleic acid and refined jojoba oil, a phytosterol, and phytosqualene. A method for producing a human sebum mimetic comprises mixing refined macadamia oil and refined jojoba oil, interesterifying the refined macadamia oil and the refined jojoba oil, adding a phytosterol alter the interesterifying, and adding phytosqualene after the interesterifying.

16 Claims, No Drawings

HUMAN SEBUM MIMETICS DERIVED FROM BOTANICAL SOURCES AND METHODS FOR MAKING THE SAME

CROSS-REFERENCES TO RELATED APPLICATIONS

This application is a divisional of U.S. patent application Ser. No. 12/911,150, filed on Oct. 25, 2010, which claims the benefit of U.S. Provisional Application No. 61/254,909, filed Oct. 26, 2009, and U.S. Provisional Application No. 61/363,564, filed Jul. 12, 2010, and incorporates the disclosure of each application in its entirety by reference. To the extent that the present disclosure conflicts with any referenced application, however, the present disclosure is to be given priority.

TECHNICAL FIELD

The present invention generally relates to personal care compositions and methods for manufacturing them, and more particularly relates to human sebum mimetics derived from botanical sources and methods for making them.

BACKGROUND

Human sebum is secreted by the sebaceous glands that are found over substantially the entire skin surface (except the palms of the hands and soles of the feet), but are found predominately on the scalp, face, chest, and back. Sebum is involved in development of the epidermal structure and maintenance of the epidermal permeability barrier, carrying antioxidants to the skin surface, protecting the skin from microbial colonization, generating body odor, and producing pheromones.

When secreted, human sebum is a complex mixture of triglycerides, wax esters, sterol esters, cholesterol, cholesterol esters, and squalene. As the sebum is secreted, it consists primarily of triglycerides and wax esters, which are broken down by commensal microbes into diglycerides, monoglycerides, and the constituent free fatty acids. The fatty acid chain lengths of human sebum vary considerably, but have predominantly 16 and 18 carbons, such as in the case of stearic acid (18 carbons with no double bond (hereinafter denoted C18:01)), oleic acid (C18:1 with one double bond on the ninth carbon (hereinafter denoted C18:1Δ9)), linoleic acid (C18:2Δ9Δ12), palmitic acid (C16:0), and sapienic acid (16:1Δ6).

Loss of human sebum can be due to a variety of environmental factors such as bathing, weather conditions, chemical products, and poor nutrition, and also can be due to genetics. For example, a natural lack of sebum is observed on the scalp of African-Americans. A loss of sebum can result in itching, dandruff, wrinkles, diaper rash and the like on the skin. In addition, the hair may become brittle and dry without a sufficient amount of sebum to moisturize it. While a variety of products exist that attempt to repair the suppleness caused by lack of sebum, many of these products contain synthetic components or components that are derived from animals and do not mimic the structure and formulation of human sebum. In this regard, the products are not absorbed by the skin as readily as human sebum. In addition, the products are often made from unstable ingredients that exhibit a short shelf life.

Accordingly, it is desirable to provide a human sebum mimetic. In addition, it is desirable to provide a human sebum mimetic produced from plant sources. It is also desirable to provide a method for manufacturing a human sebum mimetic. Furthermore, other desirable features and characteristics of the present invention will become apparent from the subsequent detailed description of the invention and the appended claims, taken in conjunction with the accompanying drawings and this background of the invention.

BRIEF SUMMARY

Human sebum mimetics and methods for producing human sebum mimetics are provided. In one exemplary embodiment, a human sebum mimetic comprises a wax ester derived from interesterification of a refined botanical oil comprising palmitoleic and refined jojoba oil, a phytosterol, and phytosqualene.

In another exemplary embodiment, a method for producing a human sebum mimetic comprises mixing refined macadamia oil and refined jojoba oil, interesterifying the refined macadamia oil and the refined jojoba oil, adding a phytosterol after the interesterifying and adding phytosqualene after the interesterifying.

In a further exemplary embodiment, a human sebum mimetic comprises a wax ester comprising a fatty acid having 16 carbons and one double bond and that is derived from a plant source, a phytosterol, and phytosqualene.

DETAILED DESCRIPTION

The following detailed description is merely exemplary in nature and is not intended to limit the invention or the application and uses of the invention. Furthermore, there is no intention to be bound by any theory presented in the preceding background or the following detailed description.

Various embodiments contemplated herein are directed to compositions that mimic human sebum. The approximate composition of human sebum includes by weight percent (wt. %) (from Pierre Agache, "Sebaceous Physiology," *Measuring The Skin*, Springer-Verlag, 2004, pp. 271-280):

| | |
|---|---|
| Squalene | 12 wt. % |
| Wax esters | 26 wt. % |
| Glycerides and free fatty acids | 57.5 wt. % |
| Sterols (free and esters) | 4.5 wt. % |

The human sebum mimetics contemplated herein are plant based, that is, the components of the mimetics are derived either physically or chemically from plant sources. In this regard, the mimetics are plant-derived analogs of human sebum in that they are derived from phytosqualene, phytosterols, a refined botanical oil such as macadamia oil, which is the source of the mimetics's triglycerides, and refined jojoba oil, which is the source of the mimetics' wax esters. As used herein, the term "refined oil" means crude oil that has had undesirable compounds such as free fatty acids, carbohydrates, metals, proteins, and the like removed using caustic agents, washing, and centrifugation. In one embodiment, the human sebum mimetic is derived from phytosqualene in an amount of about 5 to about 20 wt. % of the entire mimetic, refined jojoba oil in an amount of about 20 to about 35 wt. % of the entire mimetic, refined macadamia oil in an amount of about 45 to about 65 wt. % of the entire mimetic, and phytosterols in an amount of about 0.5 to about 10 wt. % of the entire mimetic. In a preferred embodiment, the human sebum mimetic is derived from phytosqualene in an amount of about 11 to about 15 wt. % of the entire mimetic, refined jojoba oil in an amount of about 29 to about 33 wt. % of the entire mimetic, refined macadamia oil in an amount of about 51 to about 55 wt. % of the entire mimetic, and phytosterols in an amount of about 1 to about 5 wt. % of the entire mimetic. In a more preferred embodiment, the human sebum mimetic is derived from the following composition in weight percent:

| | |
|---|---|
| Phytosqualene | 12.9 wt. % |
| Refined jojoba oil | 30.8 wt. % |
| Refined macadamia oil | 53.2 wt. % |
| Phytosterols | 3.1 wt. % |

Of its fatty acids, human sebum has particularly high levels of palmitic acid (16:0), sapienic acid (16:1Δ6), and oleic acid (C18:1Δ9). Analogously, the human sebum mimetics contemplated herein also comprise high levels of palmitic acid and oleic acid, as macadamia oil itself comprises about 8.8 wt. % palmitic acid and about 58 wt. % oleic acid. In one embodiment, the human sebum mimetic comprises about 1 to about 10 wt. % palmitic acid, in a preferred embodiment about 3 to about 7 wt. % palmitic acid, and in a more preferred embodiment about 4.8 wt. % palmitic acid. In another embodiment, the human sebum comprises about 25 to about 35 wt. % oleic acid, in a preferred embodiment about 30 to about 34 wt. % oleic acid, and in a more preferred embodiment about 31.6 wt. % oleic acid.

However, sapienic acid is unique among mammals. Palmitoleic acid (16:1Δ9), an analog of sapienic acid, is a substitute for the sapienic acid. While palmitoleic acid is fairly rare in the plant kingdom, macadamia oil has the highest palmitoleic acid content of the currently-available commercial oils, with about 16-22% palmitoleic acid. Accordingly, the inventors have found that by interesterifying the refined macadamia oil and the refined jojoba oil of the human sebum mimetic, a wax ester comprising palmitoleic acid results. While macadamia oil is preferred, other seed oils contain greater than 10% palmitoleic acid and also may be interesterified with refined jojoba oil to produce a wax ester comprising palmitoleic acid. The genera of these species include *Thunbergia, Doxantha, Alophia, Roureopsis, Telopea,* and *Asclepias.*

In one embodiment, the human sebum mimetic comprises palmitoleic acid in an amount of about 5 to about 15 wt. % of the entire mimetic composition. In a preferred embodiment, the human sebum mimetic comprises palmitoleic acid in an amount of about 8 to about 12 wt. % of the entire mimetic composition and, in a more preferred embodiment, the human sebum mimetic comprises palmitoleic acid in an amount of about 9.7 wt. % of the entire mimetic composition. In a most preferred embodiment, the human sebum mimetic comprises the following fatty acids and fatty alcohols in weight percent:

| Fatty acids: | Wt. % | Fatty Alcohols | Wt. % |
|---|---|---|---|
| Myristic acid (14:0) | 0.5 | cis-11-Eicosenaol | 5.9 |
| Palmitic acid (16:0) | 4.8 | (20:1) cis-13-docosenol | 6.3 |
| Palmitoleic acid (16:1) | 9.7 | (22:1) cis-15- | 1.9 |
| Stearic acid (18:0) | 1.9 | tetracosenol (24:1) | |
| Unknown 18:1 (18:1) | 0.1 | | |
| Oleic acid (18:1) | 31.6 | | |
| cis-Vaccenic acid (18:1) | 1.6 | | |
| Linoleic acid (18:2) | 1.3 | | |
| Linolenic acid (18:3) | 0.1 | | |
| Arachidic acid (20:0) | 1.5 | | |
| cis-11-Eicosenoic acid (20:1) | 13.9 | | |
| Behenic acid (22:0) | 0.5 | | |
| Erucic acid (22:1) | 2.9 | | |
| Lignoceric acid (24:0) | 0.2 | | |
| Nervonic acid (24:1) | 0.3 | | |

In another exemplary embodiment, the human sebum mimetics contemplated herein comprise additional functional additives, that is, an ingredient added to perform a particular function. For example, the human sebum mimetics may comprise tocopherols. In one embodiment, the human sebum mimetic comprises about 100 to about 2000 parts per million (ppm) of 70% tocopherols, preferably about 1430 ppm. The human sebum mimetics may also comprise fragrances, dyes, pigments, preservatives, antioxidants, moisturizers, and the like. By way of a further example, the human sebum mimetics may comprise emollients or thickeners, such as, FLORAESTERS 20 (FE-20) available from International Flora Technologies, Ltd. of Chandler, Ariz. FLORAESTERS 20 may be used to increase the viscosity and/or the bulk melting/dropping point of the mimetic, to more closely replicate the wax ester profile of human sebum, etc.

Alternatively, or in addition, the human sebum mimetics may be used as a component in a wide range of personal care products, such as a hair care lotions, shampoos, hair conditioners, hair gels, hair oils, hair colors, hair relaxers, hand lotions, facial lotions, eye creams, facial soaps, body lotions and creams, body scrubs, shaving gels, hair removers, sanitary wipes, and the like. Because their compositions are closely analogous to that of human sebum, the human sebum mimetics may facilitate the natural healing and recovery system of the human skin and accelerate cell turn-over and topical blood circulation, thereby decreasing the appearance of wrinkles, dark circles under eyes, and age spots. The human sebum mimetics may also reduce irritation on the scalp through natural healing and improve hydration of the skin. The human sebum mimetics could also be used beyond human application and could be used on animals and to keep fruits and vegetables fresh.

The human sebum mimetics contemplated herein are particularly suitable as substitutes for lost human sebum due to their stability. Oil stability is measured according to the American Oil Chemists Society's Official Method Cd 12b-92 at 110° C. In one embodiment, the human sebum mimetics contemplated herein have an oil stability index greater than 50 hours at 110° C. In this regard, the mimetics are substantially resistant to oxidation and have a shelf life that makes them desirable as, and in, personal care products.

In accordance with an exemplary embodiment, a method for producing a human sebum mimetic comprises mixing refined macadamia oil and refined jojoba oil, interesterifying the refined macadamia oil and the refined jojoba oil to produce a wax ester comprising a fatty acid having 16 carbons and one double bond, adding a phytosterol, and adding phytosqualene. Phytosterol can be added to the refined macadamia oil and the refined jojoba oil before interesterification and/or after interesterification. The resulting human sebum mimetic can then be bleached and/or deodorized.

In one exemplary embodiment, a mixture of 53.2 grams (g) refined macadamia oil, 30.8 g refined jojoba oil and 2.1 g phytosterol are mixed and heated to 90° C. while stirring under vacuum. After about 0.5 hours, 0.84 g sodium methoxide is added to the mixture and the temperature is increased to 130° C. and maintained at that temperature for about 2 to about 2.5 hours. The mixture is then cooled to 90° C., and 0.84 g citric acid is added with stirring for 0.5 hours. The mixture is then filtered. 1 g phytosterol and 12.9 g phytosqualene is added to the filtrate, which is mixed until homogeneity is achieved, resulting in the mimetic. 1 wt. % bleaching earth (Clarion 470 bleaching clay available from American Colloid Company, Arlington Heights, Ill.) may be added to the mimetic, which is then heated to 95° C. and maintained for 15 to 30 minutes with stirring under vacuum. The mixture is filtered. To remove odors and other volatile materials, the mimetic may be heated to 200-220° C. under high vacuum while water vapor is injected into it. The temperature is maintained for about 2 hours and then cooled while still under vacuum. In a preferred embodiment, 1430 ppm tocopherol (70%) is added and mixed into the mimetic. Any additional additives also may be added at this time.

The following are exemplary embodiments of personal care products comprising the human sebum mimetic produced as described above, with each of the components set forth in % wt/wt of the personal care product. The examples are provided for illustration purposes only and are not meant to limit the various embodiments of the human sebum mimetic in any way.

Example 1 is a hair conditioning lotion providing multiple functions including moisturizing, shining, holding, and anti-breaking functions.

EXAMPLE 1

|  | Ingredient | wt./wt. % |
|---|---|---|
| Phase A | Water | 77.95 |
|  | Polyquatemium-37 | 0.70 |
|  | Glycerin | 3.00 |
|  | SodiumPCA | 1.00 |
|  | Panthenol | 0.50 |
|  | Silicone Quatemium-8 | 2.00 |
| Phase B | Human Sebum Mimetic | 3.00 |
| Phase C | Sorbitan Stearate (and) Sucrose Cocoate | 2.00 |
| PhaseD | Propanediol | 8.00 |
|  | Quatemium 79 Hydrolyzed Keratin | 0.50 |
|  | Preservative | 1.00 |
| Phase E | Fragrance | 0.35 |
|  | Total | 100.00 |

The hair conditioning lotion of Example 1 is manufactured by heating the water to 45° C. with stirring and adding the Polyquatemium 37 with medium propeller agitation. The solution is mixed until a clear gel forms. The remaining ingredients in Phase A are added to the gel in the order listed. The ingredients in Phase B are added together at 45° C. The mixture of the Phase B ingredients is then added to the ingredients of Phase A with rapid propeller agitation. The Phase A and B ingredients are heated to 60° C. and the Phase C ingredient is added with medium propeller agitation. All ingredients of Phase D are mixed at 60° C. and are added to the Phase ABC mixture with medium propeller agitation. The resulting formula is cooled quickly on an ice-water bath. The fragrance of Phase E is then added.

Example 2 is another hair conditioning lotion providing multiple functions including moisturizing, shining, holding, and anti-breaking functions.

EXAMPLE 2

|  | Ingredient | % wt/wt |
|---|---|---|
| Phase A | Water | 71.95 |
|  | Polyquatemium-37 | 1.00 |
|  | Glycerin | 3.00 |
|  | SodiumPCA | 1.00 |
|  | Panthenol | 0.50 |
|  | Silicone Quatemium-8 | 2.00 |

-continued

|  | Ingredient | % wt/wt |
|---|---|---|
| Phase B | Ethyl Macadamiate (and) Tocopherol (and) Malic Acid | 2.00 |
|  | Human Sebum Mimetic | 3.00 |
|  | Isopropyl Jojobate (and) Jojoba Alcohol (and) Jojoba Esters | 1.00 |
|  | Phenyltrimethicone | 1.00 |
| Phase C | Sorbitan Stearate (and) Sucrose Cocoate | 2.00 |
| PhaseD | Propanediol | 8.00 |
|  | Jojoba Oil PEG-150 Esters | 1.50 |
|  | Quatemium-79 Hydrolyzed Keratin | 0.50 |
|  | Preservative | 1.00 |
|  | Hydrolyzed Jojoba Esters (and) Jojoba Esters (and) Water | 1.00 |
| Phase E | Fragrance | 0.35 |
|  | Total | 100.00 |

The hair conditioning lotion of Example 2 is manufactured using the same method as described above for Example 1.

Accordingly, human sebum mimetics and methods for producing them have been provided. The human sebum mimetics are formed from phytosqualene, phytosterols, refined jojoba oil, and a refined botanical oil, such as macadamia oil, comprising palmitoleic acid. Of its fatty acids, human sebum has particularly high levels of palmitic acid (16:0), sapienic acid (16:1Δ6), and oleic acid (C18:1Δ9). Analogously, the human sebum mimetics contemplated herein also comprise high levels of palmitic acid and oleic acid. In one embodiment, the human sebum mimetics comprise about 1 to about 10 wt. % palmitic acid and about 25 to about 35 wt. % oleic acid. However, sapienic acid is unique among mammals and rarely found in nature. The inventors have found that by interesterifying the refined macadamia oil and the refined jojoba oil of the human sebum mimetics, a wax ester comprising palmitoleic acid, a substitute for sapienic acid, results. In one embodiment, the human sebum mimetics comprise palmitoleic acid in an amount of about 5 to about 15 wt. % of the entire mimetic corn position.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention. It being understood that various changes may be made in the function and arrangement of elements described in an exemplary embodiment without departing from the scope of the invention as set forth in the appended claims.

What is claimed is:

1. A human sebum mimetic comprising:
    a wax ester derived from interesterification of:
        a refined jojoba oil; and
        a refined botanical oil comprising palmitoleic acid;
    a phytosterol; and
    phytosqualene.

2. The human sebum mimetic of claim 1, wherein the refined botanical oil comprising palmitoleic acid comprises more than 10 wt. % palmitoleic acid.

3. The human sebum mimetic of claim 1, wherein the refined botanical oil is refined macadamia oil.

4. The human sebum mimetic of claim 1, further comprising about 1 to about 10 wt. % palmitic acid.

5. The human sebum mimetic of claim 4, further comprising about 3 to about 7 wt. % palmitic acid.

6. The human sebum mimetic of claim 1, further comprising about 25 to about 35 wt. % oleic acid.

7. The human sebum mimetic of claim 6, further comprising about 30 to about 34 wt. % oleic acid.

8. The human sebum mimetic of claim 1, further comprising about 5 to about 15 wt. % palmitoleic acid.

9. The human sebum mimetic of claim 8, further comprising about 8 to about 12 wt. % palmitoleic acid.

10. The human sebum mimetic of claim 1, having an oil stability index greater than 50 hours at 110° C.

11. The human sebum mimetic of claim 1, further comprising a functional additive.

12. The human sebum mimetic of claim 11, wherein the functional additive is at least one of a tocopherol, a fragrance, a dye, a pigment, a preservative, an antioxidant, a moisturizer, an emollient, and a thickener.

13. The human sebum mimetic of claim 1, wherein the human sebum mimetic is an ingredient in a personal care product adapted for care of human or animal skin or hair.

14. The human sebum mimetic of claim 13, wherein the personal care product is a hair conditioning lotion.

15. A human sebum mimetic comprising:
   a wax ester comprising a fatty acid having 16 carbons and one double bond and that is derived from a plant source;
   a phytosterol; and
   phytosqualene.

16. The human sebum mimetic of claim 15, wherein the fatty acid comprises palmitoleic acid.

\* \* \* \* \*